United States Patent [19]

Ertle et al.

[11] Patent Number: 4,973,424
[45] Date of Patent: Nov. 27, 1990

[54] BLEACHING AND SANITIZING COMPOSITIONS

[75] Inventors: Raymond T. Ertle, Pompton Plains; Robert P. Arbaugh, Mt. Holly, both of N.J.

[73] Assignee: Capital City Products Company, Columbus, Ohio

[21] Appl. No.: 776,637

[22] Filed: Sep. 16, 1985

[51] Int. Cl.$^5$ .............................................. A62D 3/00
[52] U.S. Cl. ........................ 252/186.35; 252/186.34; 252/186.36
[58] Field of Search ..................... 252/186.35, 186.36, 252/186.34

[56] References Cited

U.S. PATENT DOCUMENTS

| | | | |
|---|---|---|---|
| 3,099,625 | 7/1963 | Gagliardi et al. | 252/186.39 |
| 3,145,206 | 8/1964 | Fuchs et al. | 252/186.35 |
| 3,336,228 | 8/1967 | Fuchs et al. | 252/99 |
| 3,350,317 | 10/1967 | Symes | 252/99 |
| 3,431,206 | 3/1969 | Hilton | 252/187.33 |
| 4,076,648 | 2/1978 | Rosen | 252/321 |
| 4,395,352 | 7/1983 | Kulkarni | 252/252 |
| 4,412,978 | 11/1983 | Ertle | 252/135 |
| 4,547,352 | 10/1985 | Ertle | 252/99 |

OTHER PUBLICATIONS

"CDB Dry Bleach Formulations", FMC Corporation Technical Publication Tech. Bulletin #131, p. 3.
"Formulating CDB Clearon", FMC Corporation Technical Publication Tech. Bulletin #128, p. 20.
"CDB Sanitizing Formulations" FMC Corp. Technical Publication, Tech. Bulletin #127, p. 9.

Primary Examiner—John Kight, III
Assistant Examiner—P. Hampton-Hightower
Attorney, Agent, or Firm—Klauber & Jackson

[57] ABSTRACT

An improved composition is disclosed for use in aqueous solution in the bleaching and/or sanitizing of fabrics. The composition comprises a polychlorinated cyanurate, which in aqueous solution provide a source of available bleaching and sanitizing chlorine; and an inhibiting system for inhibiting the activity of available chlorine from said polychlorinated cyanurate to a level beneath a predetermined fabric or fabric dye degradation level, when the concentration of said polychlorinated cyanurate is at or above saturation with respect to the aqueous solvent. The inhibiting system comprising cyanauric acid, and one or more additional salts which function to bring a 50% aqueous solution/suspension of the composition to a pH in the range of 6.1 to 7.6.

5 Claims, No Drawings

BLEACHING AND SANITIZING COMPOSITIONS

RELATED APPLICATIONS This application is a continuation-in-part of Ser. No. 458,883, filed on Jan. 18, 1983, now abandoned.

BACKGROUND OF THE INVENTION

1. Field of the Invention

This invention relates generally to the bleaching and sanitizing of fabrics and, more specifically, relates to compositions and methods for effecting such operations with reduced degradation to the fabric and/or dyes contained in the fabrics.

2. Prior Art

It has long been known in the prior art to bleach and/or sanitize fabrics with various chemical compounds which, in aqueous solution, provide a source of available chlorine. The said available chlorine is normally present in solution as hypochlorous acid or hypochlorite ion, depending upon the pH of the solution.

Among the compounds useful for such purposes are polychlorinated cyanurates. Typical polychlorinated cyanurates include sodium dichloro-s-triazine trione, potassium dichloro-s-triazine trione, and sodium dichloro-s-triazine trione dihydrate.

The polychlorinated cyanurates are normally supplied in a dry form; in the presence of sufficient water, they dissolve and react with the water, forming hypochlorous acid (HOCl) or hypochlorite ion (OCl$^-$) which is responsible for the bleaching and sanitizing actions of the compounds.

In practical use, however, these compounds have the potential to cause extensive damage to the substrates which are being bleached or sanitized, unless they are used according to a prescribed method. This prescribed method of use normally dictates a set of use conditions which eliminate the possibility of the compounds coming in contact with the substrate while in the concentrated form. For example, in the bleaching or sanitization of laundry, normally performed in a washing machine, according to the usually prescribed method of use, the compounds must be dissolved in the wash water prior to the addition of fabrics to guard against the contact of undissolved or partially dissolved particles of the bleaching compound with the fabric being laundered. This is a marked inconvenience, and requires the constant supervision of the operator to insure that no fabric damage occurs. Should the polychlorinated cyanurates or other sources of available chlorine, or formulations containing them, be poured directly onto wet fabrics in the machine under conditions of misuse, extensive damage will occur—in the form of severe dye destruction and/or fabric pinholeing.

In an effort to overcome the damage which thus occurs through the normally expected "misuse" of this type of product, formulators have gone to great lengths to encapsulate the polychlorinated cyanurates, through the use of water soluble film pouches, or agglomeration techniques, in an effort to prevent the direct contact of these compounds with the fabric. These methods are expensive, and, at best, only partially prevent the damage which invariably occurs with misuse.

It has been known for a number of years to utilize in connection with certain types of chlorine producing compositions and solutions, chlorine acceptors which are said to act as stabilizing agents. For example, U.S. Pat. No. 2,988,471 to Fuchs et al, relates to aqueous systems wherein such agents as chlorine, sodium hypochlorite, and calcium hypochlorite, are used to kill pathogenic bacteria and to prevent their growth, e.g. in potable water supplies and swimming pools. It is pointed out that while these aqueous solutions are effective bactericides and are fairly stable in the dark, they have the drawback of decomposing more or less rapidly on exposure to sunlight and in contact with metals such as iron or copper. Accordingly, Fuchs et al teaches that loss of active chlorine in such systems may be substantially reduced by adding to the aqueous solution a material such as cyanuric acid. Fuchs et al also teach the use of these stabilizing materials where the source of active chlorine, as in a swimming pool, is a compound such as sodium dichlorocyanurate.

In Hilton, U.S. Pat. No. 3,431,206, it is observed that polychlorocyanurates, while very useful as bleaching agents in connection with textiles, can cause a substantial loss of textile tensile strength and fading or yellowing of fabrics. This problem is particularly acute with respect to fabrics which have been crease-proofed by use of synthetic polymeric materials, i.e. the so-called "wash and wear" textiles or fabrics. This is said to occur because the chlorine in these bleaching agents attack the -NH groups on the polymer molecule. Hilton et al disclose that this problem can be overcome by use of certain "chlorine acceptors", including cyanuric acid. The patentees teach further, that it is preferred that the aqueous treating solution or suspension employed have a pH in the range from about 0.25 to about 10.5; also in certain embodiments, a pH from 6.5 to 9.5 is described.

Additional prior art pertinent to the present invention, include the following:

Gagliardi et al, U.S. Pat. No. 3,099,625, discloses use of certain nitrogenous organic compounds having in the molecule at least one -NH group whose hydrogen atom is labile and readily replaced by chlorine, as a chlorine acceptor where hypochlorite bleaches are used with "wash-and-wear" textiles or fabrics.

Symes, U.S. Pat. No. 3,350,317, discloses crystalline potassium containing chloro isocyanurate complex compounds and mixtures thereof, having utility in bleaching, sterilizing or disinfecting operations.

Fuchs et al, U.S. Pat. No. 3,145,206, discloses stabilizing dry alkaline metal salts of dichlorocyanuric acid against self-sustaining thermally initiated decomposition, by use, among other possibilities, of cyanuric acid in a dry state.

Fuchs et al, U.S. Pat. No. 3,336,228, disclose a dry laundry bleach which is based upon potassium dichlorocyanurate, a water-soluble alkali metal detergent builder salt in an amount sufficient to stabilize the composition, and a minor amount of an anionic organic surface active agent.

It is noteworthy that in practical use, none of the aforementioned art addresses the problem which is of central concern to the present invention, namely the potential which the aforementioned polychlorocyanurate bleaching agents have to cause extensive damage to substrates which are being bleached or sanitized, when such compositions are not used according to the manufacturer-prescribed methods aforementioned. This difficulty, which is well known to manufacturers and consumers, is sometimes addressed under the heading of "product misuse", and in the instance of bleach compositions of the type to which the present invention pertains, has extreme potential for fabric dye damage.

OBJECT OF THE INVENTION

In accordance with the foregoing, it may be regarded as an object of the present invention, to provide a composition for use in aqueous solution in the bleaching and sanitizing of fabrics, which, under conditions of misuse, will cause little or minimal damage to the fabric being treated.

SUMMARY OF THE INVENTION

Now, in accordance with the present invention, bleaching and/or sanitizing compositions have been discovered which have the unexpected property of inhibited chlorine activity at high concentrations. Using this discovery, it is, therefore, possible to formulate bleaching and sanitizing compositions which do not require special dose packaging or encapsulating techniques, and which have an extremely low potential for damaging the substrate being sanitized or bleached under conditions of misuse. Normally, the formulations of the invention only exhibit significant inhibition of the activity of the bleaching components at high concentrations, i.e., under misuse conditions, and yet allow the desirable formation of hypochlorous acid and/or hychlorite ion at normal use dilutions.

Pursuant to the invention, an improved composition for use in aqueous solution in the bleaching and sanitizing of fabrics is provided, which comprises a first component which, in aqueous solution, provides a source of available bleaching and sanitizing chlorine, and a second component comprising an inhibiting system in an effective amount to inhibit the activity of available chlorine from the first component such that fabric or fabric dye degradation is beneath a predetermined level when the concentration of the first component of the composition is above saturation with respect to the aqueous solvent. Thus, even under the striking misuse conditions wherein the powder composition is in direct contact with a wet fabric, relatively little perceptible damage to the fabric, or dye destruction, occurs.

The said first component which serves as the source of available chlorine, can comprise a polychlorinated cyanurate, including any of the said compounds which are discussed above in the "BACKGROUND" portion of this specification. The second component comprises a chlorine sink, such as cyanuric acid, with additional salts being present in the stabilizing system in amounts appropriate to adjust the pH of the finished formulation to within a specifically predetermined range at or above condition of saturation. Among the salts found useful for such purposes, alone or in combination to insure the desired pH of the finished formulation, are: sodium tripolyphosphate, sodium acid pyrophosphate, sodium citrate, sodium borate, sodium carbonate, sodium sulfate, sodium sesquicarbonate, sodium silicate, and sodium chloride.

Pursuant to this aspect of the invention, it has unexpectedly been found that minimizing damage to the fabric and dye is strikingly dependent upon providing a very narrow pH range in the composition, under the aforementioned "misuse" conditions of saturation.

The composition of the invention can also contain additional inorganic fillers and builders, provided that these ingredients do not cause the pH of the finished formulation to fall outside the desired range.

The aforementioned first component which serves as the source of available chlorine in the composition, will normally be present in sufficient concentration to provide between 0.1 and 1000 ppm available chlorine in the total wash liquor. The weight ratio between the first component i.e. the polychlorinated cyanurate, and the cyanauric acid, is generally in the range of from 1:10 to 10:1, and preferably is in the range of 1:2 to 2:1. The pH adjusting salts should be present in quantities appropriate to effect the needed pH pursuant to the invention.

DESCRIPTION OF PREFERRED EMBODIMENT

Prior art bleaching and sanitizing compositions in the field to which this invention pertains have commonly been used by the consumer by depositing quantities of same in a load of laundry or other fabrics, usually in a household washing machine. Unless the procedures for use recommended by the manufacturer of these compositions are strictly adhered to, damage to the fabrics being bleached or sanitized can readily occur. This failure (commonly by the consumer) to adhere to the instructions for proper product use, is referred to by manufacturers as product "misuse". In the most common mode of misuse, the consumer deposits the composition directly upon the fabric in the absence of sufficient water to lower the quantity of available chlorine below that at which damage occurs. For example, such compositions may be deposited upon the fabric prior to completion of the washing machine "fill" cycle. This results in a very high aqueous concentration of available chlorine, which results in fabric or dye damage.

The compositions of the present invention possess the unexpected property of precluding or minimizing damage of the foregoing type, even under the drastic conditions of misuse just specified. More specifically, under those conditions where the compositions are present at concentrations exceeding saturation with respect to the solvent, the system acts to inhibit the available chlorine, as to preclude fabric damage or fabric dye degradation.

In the present composition, the finished formulation should properly yield a pH, when measured above saturation in respect to the solvent, of between about 6.1 and 7.6.

It must be appreciated that these ranges are actually extremely narrow, since pH is a logarithmic function. It must also be noted that this range is not one normally encountered in laundry-type products, the range in the latter typically being from about 9.8 to 11.2. This latter typical range is between about 1,000 and 10,000 times more alkaline than that of the preferred embodiment of the present invention.

The invention is illustrated by the following Examples, which are considered to be illustrative only of the present invention, and should not be considered as limiting the invention which is otherwise defined in the claims:

EXAMPLE I

Samples of formulations representative of the invention, along with samples representative of formulations outside the invention, were prepared using standard mixing procedures well known to those skilled in the art. The pH of each sample was determined by employing a Perkin Elmer Metrion III pH meter along with a Corning glass electrode #476024 and a Corning Calomel ® reference electrode #476002. To prevent undesirable interactions between the chlorine containing samples and the reference electrode, a salt bridge was employed. Salt bridges were prepared by treating cotton string in the following manner: 100% cotton string having a crosssectional diameter of approximately 3 mm was cut into 6" pieces. These pieces were then boiled for 5 minutes to remove any impurities, such as sizing, from the string and, after cooling, were squeezed out by hand to remove most of the liquor. This procedure was repeated three times. The string sections were then placed in a suitable glass container and covered with a saturated solution of potassium chloride. Enough additional potassium chloride crystals were added to the jar to compensate for any plain water remaining in the strings, and to insure saturation. In actual pH determinations, the reference electrode was immersed in a beaker containing a saturated solution of potassium chloride. One end of a previously prepared salt bridge string was also immersed in this solution, and the other end of the bridge was immersed in the sample, along with the glass electrode. The salt bridge thus completed the necessary electrical connection while preventing unwanted interactions. All pH determinations were made at 25° C., employing a sample concentration of 50% by weight in water. This concentration was employed rather than the usual 1% solution since it more closely approximates the actual conditions encountered in a potential misuse situation. Since the indicated 50% by weight of the composition much exceeds the solubility of same in the water, this saturated admixture can be more properly referred to as "50% aqueous solution/suspension".

The chemical make-up of each sample formulation is listed in Table I, along with the pH determined for each sample. The polychlorinated cyanaurate used in these formulations was sodium dichloro-s-trazine trione dihydrate.

EXAMPLE II

Each sample was also subjected to a damage test. In this test, dyed cloth swatches measuring 4.5 cm×4.5 cm were each placed in the concave center of a watch glass having a diameter of 12.5 cm. The cloth was one previously selected for its tendency to exhibit dye damage when exposed to chlorine bleach. A 3 gram portion of each sample was placed in the center of a swatch, and a 10 milliliter portion of tap water at 25° C. with a hardness concentration of 50 ppm, as calcium carbonate, was carefully poured into each watch glass, care being taken not to pour the water directly on the swatch. The wetted samples were allowed to remain in intimate contact with the swatches for a period of three minutes, after which the swatches were removed from their respective watch glasses, rinsed for 30 seconds with cool tap water, and immersed in a 0.5% solution of sodium thiosulfate for a period of three minutes. The swatches were then air dried and their reflectances read on a Hunter Lab Color Difference Meter D25-2 using the L scale. Because the original white cloth has a higher reflectance than the dyed cloth, the degree of damage incurred on each swatch is indicated by a corresponding increase in reflectance.

Reflectance results along with corresponding pH values are also tabulated in Table I. The correlation of pH to damage can be readily seen from this data. A reflectance of 46 or lower, is deemed to define a pH range which is preferred in terms of correlated "damage" levels to the cloth samples. At the reflectance level of 46, most casual observers would consider damage to be barely perceptible. At a reflectance of 43, damage would not likely be judged present at the cloth sample by a casual observer. At a reflectance of about 51, such observer would consider the damage obvious. That unacceptable damage levels to the fabric can only be eliminated by operating within the very narrow pH band indicated in the Table, is a totally surprising and most unexpected finding.

TABLE I

| Sample | Parts by Weight | | | | | | | pH (50% solution/ suspension | Reflectant |
| --- | --- | --- | --- | --- | --- | --- | --- | --- | --- |
| | Polychloro- cyanurate | Cyanuric Acid | Sodium Pyro- phosphate | Sodium Tripoly- phosphate | Sodium Borate Penta- hydrate | Sodium Carbonate | Sodium Metasi- licate | | |
| A | 1.0 | 1.0 | 1.0 | — | — | — | — | 5.1 | 54 |
| B | 1.0 | 1.0 | 0.8 | 0.2 | — | — | — | 5.2 | 53 |
| C | 1.0 | 1.0 | 0.5 | 0.5 | — | — | — | 5.4 | 53 |
| D | 1.0 | 1.0 | 0.5 | 0.6 | — | — | — | 5.6 | 51 |
| E | 1.0 | 1.0 | 0.1 | 0.9 | — | — | — | 6.1 | 46 |
| F | 1.0 | 1.0 | — | 3.0 | — | — | — | 6.3 | 44 |
| G | 1.0 | 1.0 | — | 4.0 | — | — | — | 6.5 | 43 |
| H | 1.0 | 1.0 | — | — | 0.7 | — | — | 6.7 | 43 |
| I | 1.0 | 1.0 | — | — | 2.0 | — | — | 6.8 | 45 |
| J | 1.0 | 1.0 | — | — | 2.5 | — | — | 7.1 | 45 |
| K | 1.0 | 1.0 | — | — | 3.0 | — | — | 7.4 | 45 |
| L | 1.0 | 1.0 | — | — | 4.0 | — | — | 7.6 | 46 |
| M | 1.0 | 1.0 | — | — | 5.0 | — | — | 7.7 | 49 |
| N | 1.0 | 1.0 | — | — | 5.0 | 0.5 | — | 8.1 | 49 |
| O | 1.0 | 1.0 | — | — | 5.0 | 0.8 | — | 8.4 | 52 |
| P | 1.0 | 1.0 | — | — | — | 1.0 | — | 9.0 | 59 |
| Q | 1.0 | 1.0 | — | — | — | 5.0 | — | 10.0 | 60 |
| R | 1.0 | 1.0 | — | — | — | — | 2.0 | 12.2 | 63 |

While the present invention has been particularly set forth in terms of specific embodiments thereof, it is to be understood in view of the instant disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

We claim:

1. An improved dry powder composition for use in aqueous solution in the bleaching and sanitizing of fabrics, which will cause minimal fabric or fabric dye damage upon direct contact of the concentrated composition with damp or wet fabric; said composition comprising:

a first component comprising a dry polychlorinated cyanurate, which in aqueous solution provides a source of available bleaching and sanitizing chlorine; and a second component comprising an inhibiting system in an effective amount to inhibit the activity of available chlorine from the first component such that fabric or fabric dye degradation is beneath a predetermined level when the concentration of the first component of the composition is above saturation with respect to the aqueous solvent; said inhibiting system comprising cyanuric acid, and one or more additional salts which function to bring a 50% aqueous solution/suspension of said composition to a pH in the range of 6.1 to 7.6.

2. A composition in accordance with claim 1, wherein the weight ratio between said polychlorinated cyanaurate and said cyanauric acid is in the range of from 1:10 to 10:1.

3. A composition in accordance with claim 2, wherein the weight ratio between said polychlorinated cyanurate and said cyanauric acid is in the range of from 1:2 to 2:1.

4. A composition in accordance with claim 1, wherein the said additional salts are selected from one or more members of the group consisting of sodium tripolyphosphate, sodium acid pyrophospate, sodium citrate, sodium borate, sodium carbonate, sodium sulfate, sodium sesquicarbonate, sodium silicate, and sodium chloride.

5. A composition in accordance with claim 4, including additional builders.

* * * * *